(12) United States Patent
Fowler

(10) Patent No.: US 9,701,593 B1
(45) Date of Patent: Jul. 11, 2017

(54) CARBON DIOXIDE CONVERSION SYSTEM

(71) Applicant: Infinitus Renewable Energy, LLC, Plantation, FL (US)

(72) Inventor: David W. Fowler, Orange Beach, AL (US)

(73) Assignee: BB&G Environmental, LLC, Miami, FL (US)

( * ) Notice: Subject to any disclaimer, the term of this patent is extended or adjusted under 35 U.S.C. 154(b) by 0 days.

(21) Appl. No.: 15/147,522

(22) Filed: May 5, 2016

(51) Int. Cl.
| | | |
|---|---|---|
| *B01J 7/00* | (2006.01) | |
| *C07C 1/00* | (2006.01) | |
| *C07C 1/02* | (2006.01) | |
| *C07C 1/12* | (2006.01) | |
| *B01J 19/00* | (2006.01) | |
| *B01J 19/24* | (2006.01) | |

(52) U.S. Cl.
CPC .. *C07C 1/12* (2013.01); *B01J 7/00* (2013.01)

(58) Field of Classification Search
CPC .... B01J 7/00; B01J 19/00; B01J 19/24; C07C 1/00; C07C 1/02; C07C 1/12
See application file for complete search history.

(56) References Cited

U.S. PATENT DOCUMENTS

| | | | |
|---|---|---|---|
| 9,038,595 B2 | 5/2015 | Paul | |
| 2012/0252999 A1* | 10/2012 | Peters | C01C 1/18 526/340 |
| 2013/0178677 A1* | 7/2013 | Schmid | C01B 21/061 585/325 |

\* cited by examiner

*Primary Examiner* — Natasha Young
(74) *Attorney, Agent, or Firm* — Jetter & Associates, P.A.

(57) ABSTRACT

A $CO_2$ conversion system includes at least a first reactor including a gas mixing tube, a spark ignition system for generating sparks in the gas mixing tube coupled to a catalyst chamber having a catalyst therein coupled to a reaction chamber. Inlet tubes each with gas flow control valves are for injecting process gases including $O_2$, $H_2$ and $CO_2$ into the gas mixing tube, wherein the process gases react in the reaction chamber in at least one chemical reaction to form reaction products including output gases including $CH_4$ and reaction heat. A process controller utilizes at a process temperature setpoint or a criteria for an output gas to control a temperature in the catalyst chamber to maintain the process temperature setpoint or output gas criteria by adjusting gas flow control valves for changing the mass flow of at least one process gas to reduce a heat from the chemical reaction.

14 Claims, 5 Drawing Sheets

CARBON DIOXIDE CONVERSION SYSTEM

FIELD

Disclosed embodiments relate to converting carbon dioxide gas emissions from commercial industries.

BACKGROUND

Carbon dioxide ($CO_2$) is the primary greenhouse gas emitted through human activities. In 2013, $CO_2$ accounted for about 82% of all U.S. greenhouse gas emissions from human activities. $CO_2$ is naturally present in the atmosphere as part of the Earth's carbon cycle (the natural circulation of carbon among the atmosphere, oceans, soil, plants, and animals). Human activities are altering the carbon cycle—both by adding more $CO_2$ to the atmosphere and by influencing the ability of natural sinks, like forests, to remove $CO_2$ from the atmosphere. While $CO_2$ emissions come from a variety of natural sources, human-related emissions are responsible for the increase that has occurred in the atmosphere since the industrial revolution.

The main human activity that emits $CO_2$ is the combustion of fossil fuels (coal, natural gas, and oil) for energy and transportation, although certain industrial processes and land-use changes also emit $CO_2$. The main sources of $CO_2$ emissions in the United States Carbon dioxide ($CO_2$) emissions in the United States increased by about 7% between 1990 and 2013. Since the combustion of fossil fuel is the largest source of greenhouse gas emissions in the United States, changes in emissions from fossil fuel combustion have historically been the dominant factor affecting total U.S. emission trends. Changes in $CO_2$ emissions from fossil fuel combustion are influenced by many long-term and short-term factors, including population growth, economic growth, changing energy prices, new technologies, changing behavior, and seasonal temperatures. Between 1990 and 2013, the increase in $CO_2$ emissions corresponded with increased energy use by an expanding economy and population, and an overall growth in emissions from electricity generation. Transportation emissions also contributed to the 7% increase, largely due to an increase in miles traveled by motor vehicles.

Airborne $CO_2$ has come under stricter emission regulations. Reducing greenhouse gases will soon become mandatory. Separation of $CO_2$ from power plants and other commercial plants that generate large amounts of $CO_2$ is likely imminent. The cost of $CO_2$ capture is generally estimated to represent three-fourths of the total cost of a carbon capture, storage, transport, and sequestration.

A $CO_2$ removal technology that can be retrofitted into existing power plants or applied to existing storage facilities to reduce its volume is needed. A low cost $CO_2$ removal process is also needed.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments include carbon dioxide ($CO_2$) conversion systems and methods of $CO_2$ conversion that are controlled by controlling the process gas flows along with the option for multi-reactor systems to switch between reactors performing the conversion. Switching between reactors enables the $CO_2$ conversion operation to proceed in at least one reactor while cooling another reactor(s) by controlling the other reactor(s) to render it reaction-wise idle. Disclosed $CO_2$ conversion systems enable higher conversion efficiency and lower process cost as compared to known $CO_2$ conversion systems.

BRIEF DESCRIPTION OF THE DRAWINGS

Reference will now be made to the accompanying drawings, which are not necessarily drawn to scale, wherein.

DETAILED DESCRIPTION

Figure 1A:
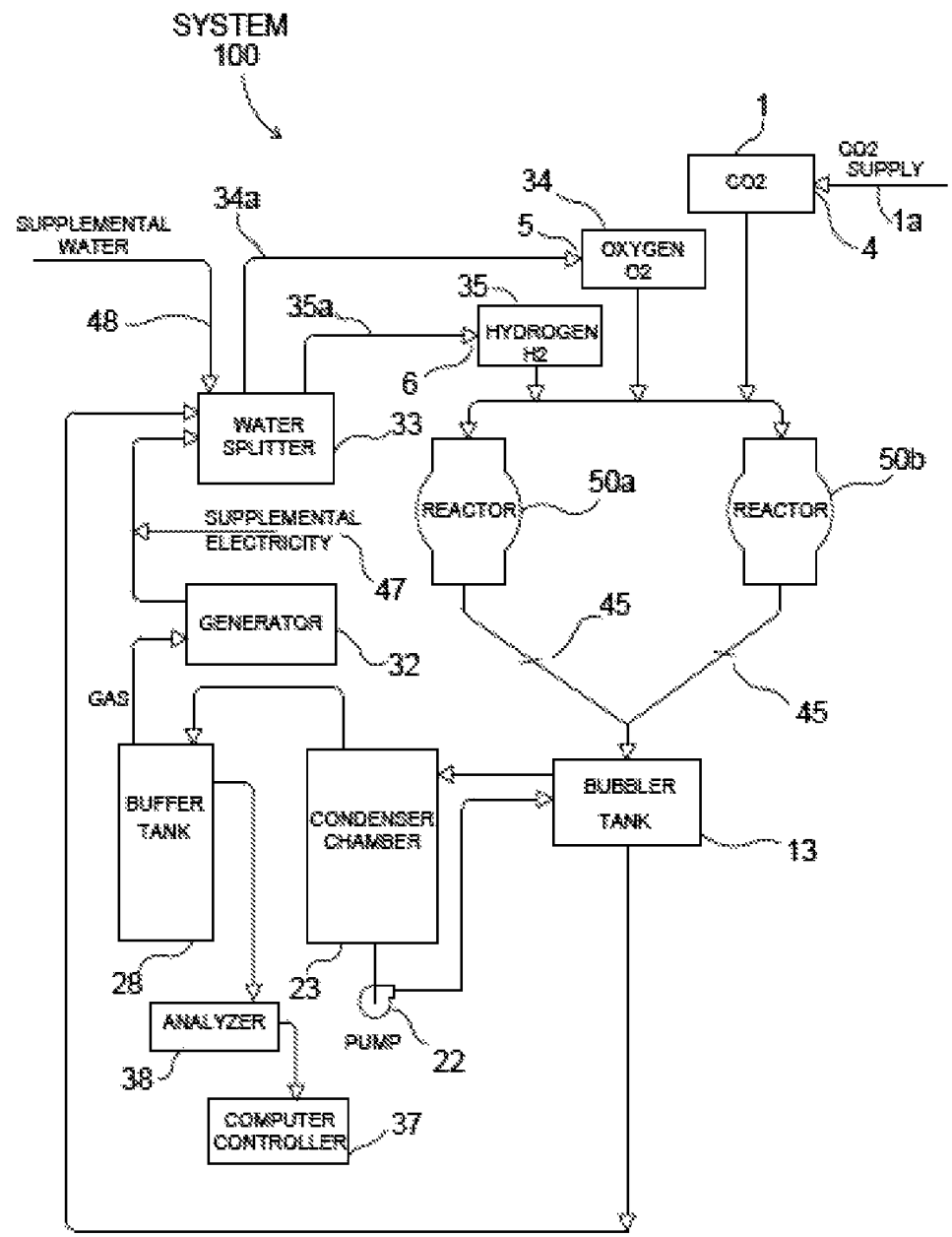
FIG. 1A shows a simplified example of a disclosed $CO_2$ conversion system including a first reactor and a second reactor that operate independently, according to an embodiment of the invention.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

The following reference numbers are used to represent disclosed features shown in the FIGs.:

1. $CO_2$
1a. $CO_2$ supply line
2. Shut off valves
3. Flow control valves
4. $CO_2$ inlet tube
5. Oxygen inlet tube
6. Hydrogen inlet tube
7. Spark plug
8. Expansion tube
8a. Gas mixing chamber
9. Temperature sensors
10. Catalyst chamber
11. Reaction chamber
12. Outlet pipe
13. Water bubbler tank
14. Level indicator
15. Water collection
16. Drain valve
17. Cooling fan
18. Cooling fins
19. Pressure indicator
20. Gas vent
21. Check valve
22. Water pump
23. Condenser chamber
24. Cooling coils
25. Chiller compressor
26. Discharge valve
27. Gas pump
28. Buffer tank
29. Pressure regulator
30. By-pass valve
31. Piping
32. Generator
33. Water splitter
34. Oxygen ($O_2$)
34a. $O_2$ supply line
35. Hydrogen ($H_2$)
35a. $H_2$ supply line
36. Supplemental power
37. Computer controller
38. Continuous gas analyzer
39. Spark transformer
40. Flange connection
41. Orphic plate
42. Pressure restriction
43. Catalyst
44. Screen plate
45. Check valve
46. Power switch controller
47. Supplemental electricity
48. Supplemental water supply
50a. First reactor system
50b. Second reactor system Disclosed $CO_2$ conversion systems remove $CO_2$, such as from the environment, including $CO_2$ emitted from commercial industries. A variety of industries are now faced with the issue of reducing $CO_2$ emissions into the atmosphere. The chemical reactions for disclosed $CO_2$ conversion processes are generally not new, but disclosed conversion systems include several new control features then enable both higher conversion efficiency and lower process cost.

The efficiency of disclosed $CO_2$ conversion systems is increased by regulating the process temperature through control of the process gas flows along with the option in multi-reactor systems to switch between reactors to operate one reactor(s) while cooling another reactor(s) by controlling it to render it idle reaction-wise. In addition, the conversion system itself can supply the majority of the power utilized for the conversion process which can reduce the process cost. The result is a scalable system design that has a wide variety of industrial applications. The system design is based on the Sabatier reaction which through control of the process gas flows can switch between the Sabatier reaction and Bosch reaction while running.

In the conventional Sabatier reaction (sometimes referred to as the "Global Reaction"). $CO_2$ is converted to $CH_4$ (methane) in the presence of hydrogen ($H_2$) gas. This Sabatier reaction can be represented by:

$$CO_2 + 4H_2 \rightarrow CH_4 + 2H_2O$$

The Bosch reaction is a chemical reaction between $CO_2$ and $H_2$ that produces elemental carbon (graphite), water, and about a 10% return of the 'invested' heat. The Bosch reaction involves the introduction of iron as a catalyst and a temperature level of about 530° C. to 730° C.

The overall Bosch reaction is as follows:

$$CO_2 + 2H_2 \rightarrow C(s) + 2H_2O$$

The Bosch reaction is the result of two chemical reactions. The first chemical reaction, the reverse water gas shift reaction, is a relatively rapid one:

$$CO_2 + H_2 \rightarrow CO + H_2O$$

The second chemical reaction is a slower one which controls the reaction rate:

$$CO + H_2 \rightarrow C(s) + H_2O$$

The overall Bosch reaction produces about $2.3 \times 10^3$ joules for every gram of $CO_2$ reacted at 650° C. Reaction temperatures are generally in the range of 450° C. to 600° C. The Bosch reaction can be accelerated in the presence of an iron, cobalt or a nickel catalyst. Ruthenium (Ru) can also be the catalyst to speed up the Bosch reaction.

FIG. 1A shows a simplified example of a disclosed $CO_2$ conversion system 100 including a first reactor 50a and a second reactor 50b that operate independently, according to an embodiment of the invention. No flow control features are shown in FIG. 1A except for check valves 45 for simplicity (see FIG. 1B described below which shows flow control features). Although system 100 has two reactors 50a and 50b, disclosed $CO_2$ conversion systems can have a single reactor, or three or more reactors. The process gases utilized comprises $CO_2$ 1 that is supplied to the reactors 50a, 50b of the $CO_2$ conversion system 100 through a $CO_2$ supply line 1a coupled to a $CO_2$ inlet tube 4 along with oxygen ($O_2$) 34 supplied through an $O_2$ supply line 34a coupled to an $O_2$ inlet tube 5, and $H_2$ 35 supplied through a $H_2$ supply line 35a coupled to a $H_2$ inlet tube 6. The output of the reactors 50a and 50b are coupled to a water collection bubbler tank (water bubbler tank) 13. Discharge gas back flow between the reactors 50a and 50b is prevented by a check valve 45 provided at each reactor's outlet section that enables the first reactor 50a and a second reactor 50b to operate independently.

A condenser chamber 23 including cooling coils (not shown) has an input coupled to an output of the water bubbler tank 13. A buffer tank 28 has an input coupled to an output of the condenser chamber 23. Pump 22 pumps water from the bottom of the condenser chamber 23 into the water bubbler tank 13. The water splitter 33 is coupled to receive power from an electrical generator 32 and optional power from a supplemental electricity (source) 47, as well as water from the water bubbler tank 13 and optional supplemental water from supplemental water supply 48 for splitting the water to generate $O_2$ and $H_2$. Gas supply lines 34a and 35b couple an output of the water splitter 33 to inlet tubes 5, 6 to deliver the $O_2$ 34 and $H_2$ 35 to the reactors. The electrical generator 32 is coupled to receive gas (including methane ($CH_4$)) from the buffer tank 28 and as noted above is coupled to provide the power it generates to at least partially power the water splitter 33. A continuous gas analyzer (analyzer) 38 is also shown coupled to the buffer tank 28, and a controller 37 shown as a "computer controller" (e.g., a programmable logic controller (PLC)) is coupled to receive the analyzer output from the analyzer 38.

Figure 1B:
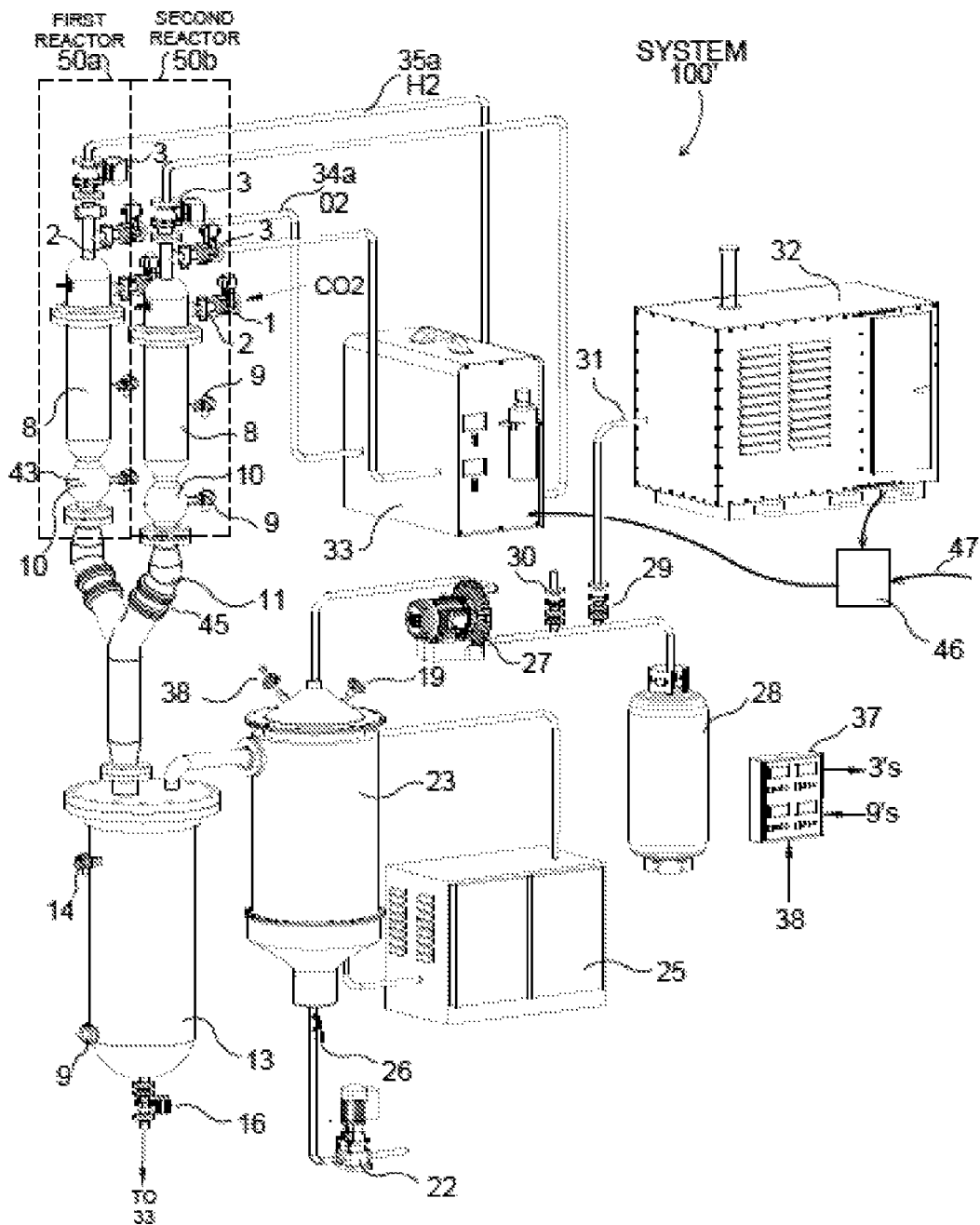
FIG. 1B shows example details including flow control features for the $CO_2$ conversion system shown in FIG. 1A, according to an embodiment of the invention.

FIG. 1B shows example details including flow control features for the $CO_2$ conversion system 100 shown in FIG. 1A now shown as system 100', including control details for independently operating the first reactor 50a and second reactor 50b to provide the option to switch between reactors for cooling purposes, accord to an example embodiment. The process gases utilized comprises $CO_2$ 1 (such as emitted from a combustion process occurring at a hydrocarbon-based electricity generation plant) that is supplied to the conversion system 100' along with $O_2$ 34 and $H_2$ 35. The gas flow control valves 3 are controlled by the controller 37 to regulate and blend the incoming process gases flowing into the expansion tube 8. The flow control valves 3 may comprise mass flow controllers. Shut off valves 2 are also provided in the respective reactant lines.

The controller 37 also monitors and records pressures levels (from pressure sensor 19), temperatures (from temperature sensors 9) and the composition of outlet gass(es) along with the collected water level provided by the 38 that is coupled to sense the gases within the condenser chamber 23. $O_2$ 34 and $H_2$ 35 are combined in the gas mixing chamber 8a within the expansion tube 8 with the incoming $CO_2$ 1 for the main $CO_2$ conversion process. The startup procedures involve the catalyst (see catalyst 43 in catalyst chambers 10 in FIG. 2 described below) being preheated for the $CO_2$ conversion reaction to start. The catalyst 43 can comprise certain metals such as iron, cobalt, nickel or ruthenium.

At start-up, $O_2$ 34 combined with $H_2$ 35 is ignited in the gas mixing chamber 8a by a spark from a spark source such as a spark plug 7 driven by a spark transformer 39 to provide the initial heat needed to activate the catalyst 43 in the catalyst chamber 10. When the temperature sensor 9 in the gas mixing chamber 8a indicates that a particular temperature set point has been reached, the controller 37 is programmed to act so that $O_2$ 34 is removed from the gas flow and is substituted by $CO_2$ 1.

In the presence of the catalyst 43 that is heated (e.g., 550° C.) by the heat generated from forming water, oxygen is disassociated from the $CO_2$ which then combines with $H_2$ 35 in the reaction chamber 11 to form $H_2O$. The carbon (C) from the disassociated $CO_2$ combines with $H_2$ 35 to form methane ($CH_4$). This is recognized as the Sabatier reaction which is an exothermic reaction that is used to supply some of the heat needed to maintain the temperature for the catalyst 43. However, it is recognized that excessive heat buildup can reduce the efficiency of the Sabatier reaction. Therefore the temperature of the reaction is generally controlled to be limited by the $CO_2$ conversion system 100 by switching between the first reactor 50a and the second reactor 50b to allow one reactor to be idle reaction-wise to cool to a selected temperature set point while the other reactor is operating as a $CO_2$ converter.

Known cooling designs in contrast for chemical reactors use a water jacket or other types of heat exchangers to control the reaction heat. Heat exchanger temperature control is recognized to remove heat from the reactor surfaces only, and is not as effective for cooling the catalyst 43 which is internal to the system being inside the catalyst chamber 10. As described above, disclosed $CO_2$ conversion systems utilize a cooling design that controls the incoming processes gas flows to control the reaction temperature along with the ability to divert the conversion process to another reactor. By removing essentially all the $CO_2$ and $H_2$, and adding only $O_2$ 34 back to the reactor, heat is removed which cools the catalyst 43.

In one embodiment the controller 37 can monitor the temperature of the catalyst 43 using a temperature reading from a temperature sensor 9 in the catalyst chamber 10 to implement proportional-integral-derivative (PID) process control. This allows for precise temperature control and uniform catalyst exposure temperatures, prevents hotspots, and allows the catalyst 43 to function more efficiently. As noted above, feeding $O_2$ 34 alone (no $H_2$) into the reactor(s) 50a, 50b allows for heat to be removed from the catalyst 43 without any exothermic reaction, evenly cooling the catalyst 43. By switching on only $O_2$ 34 for a cooling media a close temperature set point can be maintained which can be combined with switching between reactors 50a and 50b converting $CO_2$ to implement a cooling process, so that continuous consumption of $CO_2$ is provided by the $CO_2$ conversion system.

The controller 37 utilizes at least one of a process temperature set point and a criteria for at least one of output gas to control the temperature in the catalyst chamber to maintain the process temperature set point or output gas criteria by adjusting a mass volume flow of at least one process gas, such as using gas flow control valves 3 to reduce a heat from the chemical reaction. The output gas criteria can be based on three different example conditions that can exist at the reactor's gas discharge.

1. The $H_2$ discharge is too high. Here the output indicates a high level of unreacted $H_2$ which generally means the gas ratio is off, the temperature is too low or the catalyst exposure is too low. The correction can be to reduce the $H_2$ flow, increase the $CO_2$ flow to allow for more reaction between the split O2 and H2, or dropping the flow rate to allow for more time for catalyst exposure.

2. The $CO_2$ discharge is too high. Here the output indicates a high level of un-cracked $CO_2$, which generally means the gas ratio is off, the catalyst temperature is too low, or the catalyst exposure time is too low. The correction can be to reduce the $CO_2$ flow, increase the $H_2$ flow to allow for more reaction between the split oxygen and $H_2$, or dropping the flow rate to allow for more time for catalyst exposure.

3. The $CH_4$ discharge is dropping. This generally indicates too high a temperature and the Bosch reaction is taking place. A high level of CO and a low level of $CH_4$ with a low level of $H_2$ is being discharged. The correction can be to switch to the other reactor to allow the catalyst temperature to drop back to a catalyst temperature set point.

Any combination including all three of these conditions in one particular embodiment can be compared by a computer program implemented by controller 37 to decide on the best corrective action. The volume flow rate, along with the catalyst temperature are compared with the discharge gases being indicated and the calculated action can thus be controlled.

The output production of $CO_2$ conversion is based on parameters including the process gas mix ratio, the temperature of the catalyst 43, and the internal pressure in the reactors 50a and 50b. These all can be controlled by the controller 37 which monitors the temperatures and pressures, as well as the gas quality being supplied to the buffer tank 28 that supplies combustible gas including $CH_4$ for the generator 32. The output gas is monitored with the analyzer 38 sampling the gas in the condenser chamber 23 after all the water vapor generated has been condensed. If there is a need for a different gas input mixture to meet the output gas settings generally programmed into the controller 37 (such as the $H_2$ to $O_2$ ratio for generating more or less reaction heat), then the controller 37 can send a control signal for adjusting the mix volume ratio of one or more of the process gases (1, 34, 35) input via their respective flow control valves 3.

The pressure in the reactors 50a and 50b can be regulated by delaying the ignition and allowing the process gases to build up in the gas mixing chamber 8a. When increased pressure is desired, a mixture of $O_2$ 4 and $H_2$ 35 can be introduced without the spark being present. This delay before ignition causes the gases to build in the gas mixing chamber 8a and then rapidly expand when ignited causing both heat and pressure to be applied to the catalyst 43 creating a "popping" effect that can be accelerated or decelerated. As noted above, the fuel generated such as methane can be used by generator 32 to generate electricity for the process of generating $H_2$ and $O_2$. As the gases flow through the catalyst 43, $H_2$ 35 and $CO_2$ 1, during $CO_2$ dissociation the oxygen from $CO_2$ 1 is pulled away from the carbon. An orifice plate 41 (see FIG. 2) having a small aperture in expansion tube 8 restricts the gas expansion and creates pressure in the expansion tube 8. Heat and pressure help with $CO_2$ separation. The orifice plate 41 also regulates the gas flow rate to the catalyst 43. This feature allows for more reaction time in the reactor chamber 11, which can raise the $CO_2$ conversion efficiency.

The $H_2$ 35 first comes in contact with the $O_2$ in the gas mixing chamber 8a creating $H_2O$. The excess $H_2$ 35 is then combined with the loose carbon creating $CH_4$ (methane). As noted above, the methane generated can then be used as fuel for the electrical generator 32 that provides at least a portion of the electrical power for the water splitter 33 (see FIG. 3 described below) which splits water to generate the $O_2$ 34 and $H_2$ 35 needed for the $CO_2$ conversion process. If excessive heat is built up in the catalyst chamber 10, an external cooling fan 17 can push air across the cooling fins 18 (both shown in FIG. 3) to reduce the heating as needed if a run-away heating is indicated by the temperature sensor 9. Moreover, the use of a second reactor allows for cooling of the non-used reactor which helps maintain the $CO_2$ conversion system having continuous $CO_2$ conversion operation.

The remaining (unreacted) gases of $H_2$ 35 and carbon travel through the reactor chamber 11 having an enlarged diameter to slow the gas velocity down to provide additional reaction time. The reactor chamber 11 will generally be heavily thermally insulated to retain heat. At this point the resultant gases flow flows through an outlet 12 (see FIG. 3 described below) into a water bubbler tank 13. The water that is generated from the hydrogen/oxygen reaction is directed by gravity to be collected at the bottom 15 of the water bubbler tank 13. The water in the water bubbler tank 13 will build over time in both volume and heat. A level indicator 14 controls the level of water by releasing water collected at the bottom 15 of the water bubbler tank 13 through a discharge valve 16 where it can be used in the water splitter 33 which is shown in FIG. 1B generating both the $O_2$ 34 and $H_2$ 35.

Figure 3:
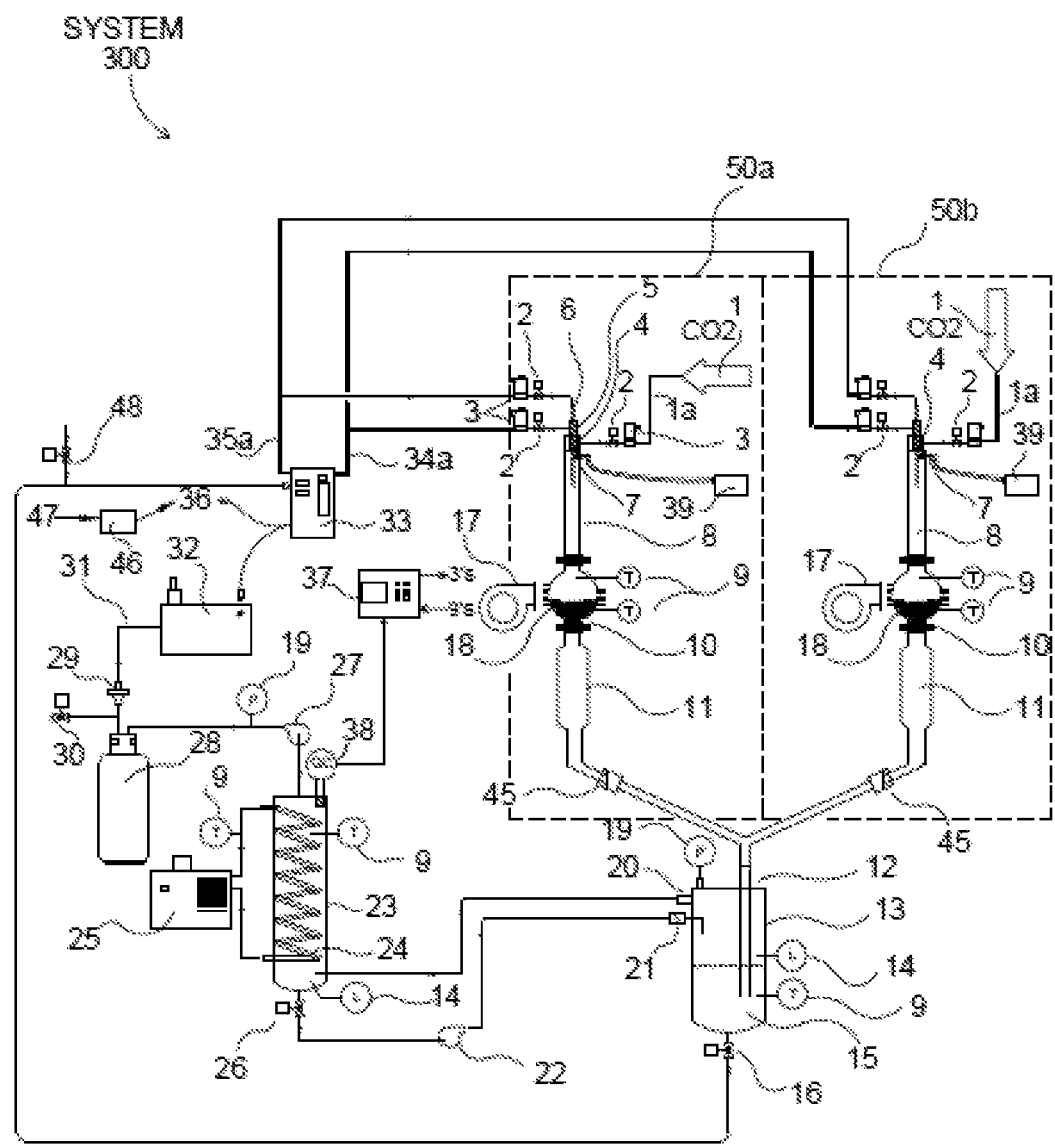
FIG. 3 is another view of the $CO_2$ conversion system shown in FIG. 1B that shows additional features including internal features such as cooling coils in the condenser chamber and water in the water bubbler tank, according to an embodiment of the invention.

As shown in FIG. 3 the temperature of the water in the water bubbler tank 13 is controlled by a chilled water pump 22. The chilled water pump 22 returns chilled water into the water bubbler tank 13 through a check valve 21 that overcomes back pressure. This chilled water is the discharge steam coming from the water bubbler tank 13 through an exit port 20 into the condenser chamber 23. Water vapor and steam are condensed inside condenser chamber 23 which drips to a discharge valve 26. This is performed by a cooling coil 24 that circulates an ethylene glycol mixture (or other heat-transfer fluid) that passes through a chiller compressor 25. This heat exchange is monitored by a temperature sensor 9 to prevent the water from freezing which can plug the system.

The level indicator 14 inside the condenser chamber 23 can indicate a buildup of water is pumped into the water bubbler tank 13 where the water in the water bubbler tank 13 is mixed with the relatively cooler incoming water received from the condenser chamber 23. Gases flowing out of the water bubbler tank 13 through the condensing chamber 23 are pumped by a pump 27 into a buffer tank 28 where it is allowed to be redirected for use. The pump 27 pulls the gases from the condensing chamber 23 into the buffer tank 28. The gases (including $CH_4$) then flow from the output of the buffer tank 28 through a pressure regulator 29 then piping 31 into a generator 32 that provides electrical power to the water splitter 33 which generates both the $O_2$ 34 and $H_2$ 35 needed for the $CO_2$ conversion process. If auxiliary power is needed for production of the $H_2$ and $O_2$, an auxiliary power input from an auxiliary power generator 36 can provide for this need. A by-pass valve 30 is shown between the output of the pump 27 and the pressure regulator 29.

Figure 2:
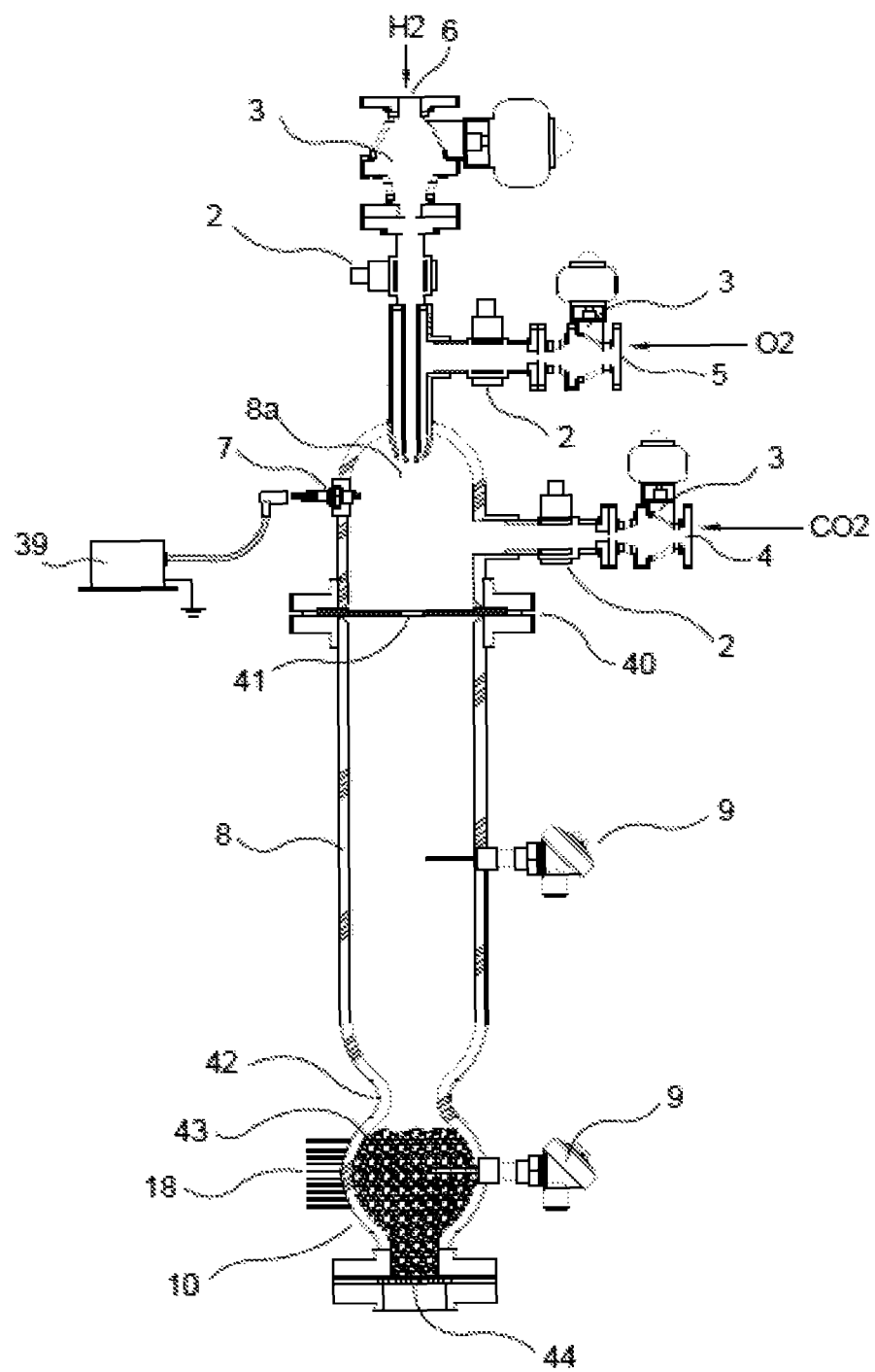
FIG. 2 shows details for an example expansion tube coupled to a catalyst chamber of an example reactor chamber, according to an embodiment of the invention.

FIG. 2 shows details for an example expansion tube 8 having its gas mixing chamber 8a coupled to a catalyst chamber 10, according to an embodiment of the invention. As noted above, reference 4 is a $CO_2$ inlet tube. A spark transformer 39 is shown coupled to a spark plug 7 for generating a spark within the gas mixing chamber 8a, a flange connection 40 is also shown that allows an orifice plate 41 to be within the expansion tube 8, and a pressure restriction 42 in the form of a tube narrowing is shown at the bottom of the expansion tube 8. At the bottom of the catalyst chamber 10 a screen plate 44 is shown to retain the catalyst.

FIG. 3 is another view of the $CO_2$ conversion system 100' shown in FIG. 1B now shown as system 300 that includes additional features including internal features such as cooling coils 24 in condenser chamber 23 and water in the water bubbler tank 13. A gas supply from the buffer tank 28 to the generator 32 is shown coupled by piping 31. The water splitter 33 is shown being powered by the generator 32 supplemented by outside source electrical power 47 controlled by a power switch controller 46. Check valves 45 are shown between the reactor chambers 11 and the water bubbler tank 13 which also prevents discharge gas back flow between the reactors 50a and 50b.

Disclosed embodiments include a method of $CO_2$ conversion. The method comprises providing a $CO_2$ conversion system including at least a first reactor including an expansion tube coupled to a catalyst chamber having a catalyst therein that is coupled to a reaction chamber. A mixture of process gases comprising $O_2$, $H_2$ and $CO_2$ are injected into the expansion tube 8 together with a spark, wherein the process gases react in the reaction chamber 11 in at least one chemical reaction to form reaction products comprising output gases including CH$_4$ and reaction heat. Using a process controller utilizing at least one of a process temperature set point and a criteria for at least one of the output gases (output gas criteria), a temperature in the catalyst chamber is controlled to maintain the process temperature set point or output gas criteria by adjusting a mass flow of at least one of the process gases to reduce a heat from the chemical reaction.

The adjusting the flow can be based on gas analyzer readings of the reaction products compared to the output gas criteria. The method can further comprising controlling a pressure in a gas mixing chamber 8a of the expansion tube 8 by controlling intervals of time the spark is present in the gas mixing chamber 8a of the expansion tube 8. The method can further comprising coupling the CH$_4$ into a power generator 32, where the power generator provides electrical power to power a water splitter 33 that supplies both the O$_2$ and H$_2$ to the gas mixing chamber 8a of the expansion tube 8. The adjusting of flow can convert the chemical reaction from a Sabatier reaction to a Bosch reaction while continuously running the method.

The method can further comprise analyzing the output gases, wherein the process controller using a result of the analyzing maintains mix volumes and the process temperature set point, and using an efficiency of the catalyst can triggers reactor switching between the first reactor and second reactor to efficiency of the CO$_2$ conversion system. The analyzer 38 can maintain mix volumes and temperatures and its data provided used to recognize the efficiency of the catalyst to trigger the reactor switch between reactors to maintain flow and CO2 conversion efficiency.

EXAMPLES

Figure 4:
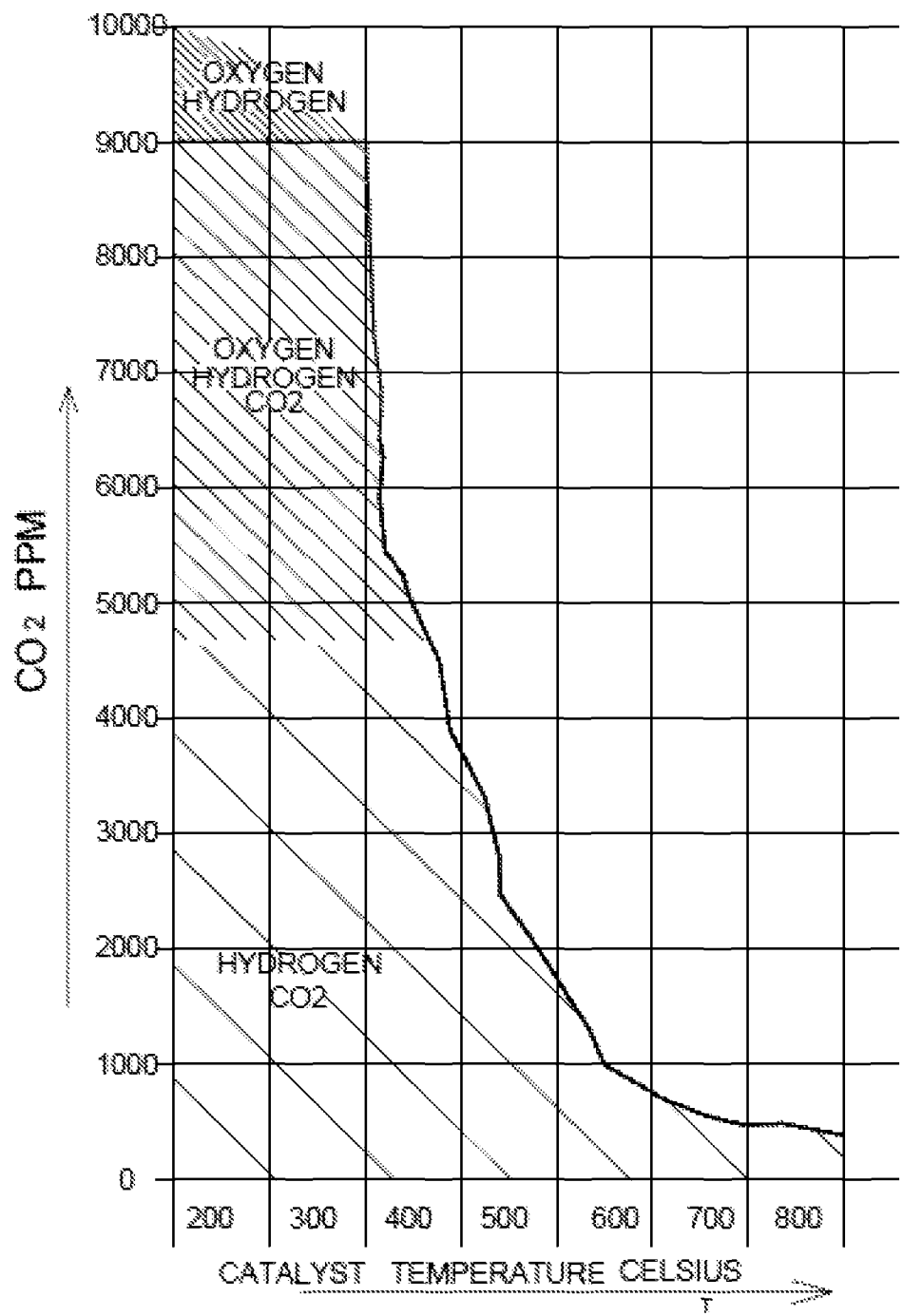
FIG. 4 is test data from a disclosed $CO_2$ conversion system showing a plot of $CO_2$ (in ppm) vs. the catalyst temperature.

Disclosed embodiments are further illustrated by the following specific Examples, which should not be construed as limiting. FIG. 4 is test data from a disclosed CO$_2$ conversion system showing a plot of CO$_2$ (in ppm) vs. the catalyst temperature. A smart relay was used to control the solenoid valves that was programmed to open each gas valve on demand. Each gas was tested to the volume calculated to meet the design results. A water displacement method was used to set each gas (H$_2$, O$_2$ and CO$_2$) flow. A tube was placed under water inside a filled glass. The glass volume was calculated based on the diameter and length. A smart relay pulsed one second open and the gas displacement was measured. A needle valve was used to adjust the volume per pulse of the gas until the rate was achieved. This was repeated for each gas. A stainless chamber was used to simulate the reactor design. The catalyst was placed downstream of the gas inlets.

The gas discharge included a screen and tube connected to a water bubbler. The tube between the water bubbler was about 5 feet long to help in cooling the discharge gas to condense. The bubbler jar was connected to a gas separation tank to allow any extra H$_2$ to float out, leaving the heaver CH$_4$ to remain in the tank. The finial vent port was monitored with a CO$_2$ meter that calculated the PPM and percent ratio of CO$_2$. To start the reaction, as noted above, heat is needed for the catalyst. H$_2$ and O$_2$ were introduced into the reactor and a spark was ignited to light the gases. This was continued into the catalyst to reach a temperature of about 500° F. minimum. A thermocouple inside the catalyst was used to report the temperature. CO$_2$ was then introduced to check if the catalyst temperature started to climb. If the temperature went down, it was determined that the catalyst was catalyzing a reaction.

At that point the CO$_2$ was stopped and the H$_2$ and O$_2$ hydrogen and oxygen were allowed to ignite together and drive the catalyst to climb in temperature. The heat from the H$_2$ and O$_2$ was pushed into the catalyst from above. As the heat would build in the catalyst, then CO$_2$ was then again introduced. If the catalyst temperature started to climb, the O$_2$ and spark was stopped. The catalyst at this point cracked the CO$_2$ and the H$_2$ reacted with the split oxygen from the CO$_2$ and ignited inside the catalyst. The heat was now directly inside the catalyst and drove the heat up very rapidly. The heat was controlled by denying CO$_2$. It was also tested by adding O2 and denying H$_2$. By allowing the temperature go to a higher state the Bosch reaction took effect. This was proven by the low CO$_2$ PPM count found at the discharge. The startup CO$_2$ count (before the heat was reached) was over 9,000 PPM and started dropping after 200° C. was reached.

As shown in FIG. 4, as the temperature went up the CO$_2$ concentration in PPM went down. As shown in FIG. 4, at 500° C. the CO$_2$ concentration was found to drop to about 2,500 ppm, and at 700° C. the CO$_2$ concentration was found to drop to about 500 ppm where a balance (no significant change in CO$_2$ concentration with a change in temperature) was reached.

A catch sample was taken of the discharge gas and burned to check for the type of gas. If the burn test was a quick, sharp "pop" it indicated H$_2$ as the collected fuel. If the burn test showed a low or no burn, it was H$_2$ or CH$_4$ mixed with CO2, where the CO$_2$ would dilute the mixture. If it was a high yellow burn, it indicated CH$_4$ gas was collected. The burn test indicated CH$_4$, due to the yellow flame and lower combustion sound. A second burn test was preformed to prove the presence of CH$_4$. The discharge gas was collected in a container and the container was set up right with the lid removed and allowed to set for 30 seconds. This allowed the lighter than air H$_2$ float out of the container and then ignite the container. A high volume of low tone, yellow flame was shown, proving the presence of appreciable CH$_4$.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The invention claimed is:

1. A method of carbon dioxide (CO$_2$) conversion, comprising:
   providing a CO$_2$ conversion system including at least a first reactor including an expansion tube coupled to a catalyst chamber having a catalyst therein that is coupled to a reaction chamber;
   injecting a mixture of process gases comprising O$_2$, H$_2$ and CO$_2$ into said expansion tube together with a spark, wherein said process gases react in said reaction chamber in at least one chemical reaction to form reaction products comprising output gases including CH$_4$ and reaction heat, and using a process controller utilizing at least one of a process temperature set point and a criteria for at least one of said output gases (output gas criteria), controlling a temperature in said catalyst chamber to maintain said process temperature set point or said output gas criteria by adjusting a mass flow of at least one of said process gases using gas flow control valves to reduce a heat from said chemical reaction.

2. The method of claim 1, wherein said adjusting said mass flow is based on gas analyzer readings of said reaction products compared to said output gas criteria.

3. The method of claim 1, further comprising controlling a pressure in a gas mixing chamber by controlling intervals of time said spark is present in said gas mixing chamber.

4. The method of claim 3, further comprising coupling said $CH_4$ into a power generator, said power generator providing electrical power to power a water separator system that supplies both said $O_2$ and said $H_2$ to said gas mixing chamber.

5. The method of claim 1, wherein said adjusting said mass flow converts said chemical reaction from a Sabatier reaction to a Bosch reaction while continuously running said method.

6. The method of claim 1, wherein said at least a first reactor comprises said first reactor and at least a second reactor, and wherein said adjusting said mass flow further comprises switching conversion operation between said first reactor and said second reactor while maintaining continuous consumption of said $CO_2$.

7. The method of claim 1, further comprising analyzing said output gases, wherein said process controller using a result of said analyzing maintains mix volumes for said process gases and said process temperature set point, and using an efficiency of said catalyst triggers reactor switching between said first reactor and said second reactor providing said $CO_2$ conversion to raise a $CO_2$ conversion efficiency of said $CO_2$ conversion system.

8. A carbon dioxide ($CO_2$) conversion system, comprising:
at least a first reactor including an expansion tube including a spark ignition system coupled to a spark plug for generating a spark in a gas mixing chamber of said expansion tube coupled to a catalyst chamber having a catalyst therein that is coupled to a reaction chamber;
inlet tubes each with gas flow control valves for injecting process gases comprising $O_2$, $H_2$ and $CO_2$ into said expansion tube, wherein said process gases react in said reaction chamber in at least one chemical reaction to form reaction products comprising output gases including $CH_4$ and reaction heat, and
a process controller utilizing at least one of a process temperature set point and a criteria for at least one of said output gases (output gas criteria) for controlling a temperature in said catalyst chamber to maintain said process temperature set point or said output gas criteria by adjusting a mass flow using said flow control valves for changing a mass flow of at least one of said process gases to reduce a heat from said chemical reaction.

9. The $CO_2$ conversion system of claim 8, further comprising:
a water collection bubbler tank (water bubbler tank) coupled to an output of said reaction chamber;
a condenser chamber including cooling coils having an input coupled to an output of said water bubbler tank;
a buffer tank having an input coupled to an output of said condenser chamber;
a water splitter coupled to receive water from said water bubbler tank for splitting said water to generate said $O_2$ and said $H_2$;
gas supply lines coupling an output of said water splitter to said inlet tubes to deliver said $O_2$ and said $H_2$ to said inlet tubes, and
an electrical generator couple to receive gas from said buffer tank including said $CH_4$ and coupled to provide electrical power it generates to said water splitter.

10. The $CO_2$ conversion system of claim 8, further comprising an orifice plate having an aperture in said expansion tube for restricting expansion of said process gases to create additional pressure in said expansion tube.

11. The $CO_2$ conversion system of claim 8, wherein said adjusting said mass flow performed by said process controller is based on output gas analyzer readings of said reaction products compared to said output gas criteria.

12. The $CO_2$ conversion system of claim 8, wherein said adjusting said mass flow performed by said process controller converts said chemical reaction from a Sabatier reaction to a Bosch reaction while in continuous conversion operation of said $CO_2$ conversion system.

13. The $CO_2$ conversion system of claim 8, wherein said at least a first reactor comprises said first reactor and at least a second reactor, wherein said adjusting said mass flow performed by said process controller further comprises switching conversion operation between said first reactor and said second reactor while maintaining continuous consumption of said $CO_2$.

14. The $CO_2$ conversion system of claim 8, further comprising a continuous gas analyzer for analyzing said output gases, and said process controller using a result of said analyzing maintains mix volumes for said process gases and said process temperature set point, and using an efficiency of said catalyst triggers reactor switching between said first reactor and said second reactor providing said $CO_2$ to raise a $CO_2$ conversion efficiency of said $CO_2$ conversion system.

* * * * *